(12) United States Patent
Ito et al.

(10) Patent No.: US 10,298,174 B2
(45) Date of Patent: May 21, 2019

(54) PHOTOELECTRIC CONVERSION ELEMENT EVALUATION APPARATUS

(71) Applicant: Yokogawa Electric Corporation, Tokyo (JP)

(72) Inventors: Akishige Ito, Tokyo (JP); Masato Ishikawa, Tokyo (JP); Takashi Tsubota, Tokyo (JP); Yoshinori Matsumoto, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 527 days.

(21) Appl. No.: 14/992,492

(22) Filed: Jan. 11, 2016

(65) Prior Publication Data
US 2016/0248375 A1 Aug. 25, 2016

(30) Foreign Application Priority Data
Feb. 24, 2015 (JP) .................... 2015-033956

(51) Int. Cl.
*H02S 50/15* (2014.01)
*G01N 21/17* (2006.01)
*H02S 50/10* (2014.01)

(52) U.S. Cl.
CPC ......... *H02S 50/15* (2014.12); *G01N 21/1717* (2013.01); *H02S 50/10* (2014.12); *G01N 2021/1719* (2013.01); *G01N 2021/1725* (2013.01)

(58) Field of Classification Search
CPC ...... H02S 50/15; H02S 50/10; G01N 21/1717
See application file for complete search history.

(56) References Cited

U.S. PATENT DOCUMENTS

| 4,211,488 A * | 7/1980 | Kleinknecht ........ G01N 21/314 250/559.16 |
| 2004/0196464 A1* | 10/2004 | Akutsu .............. G01N 21/1717 356/432 |

(Continued)

FOREIGN PATENT DOCUMENTS

| EP | 2 863 539 A1 | 4/2015 |
| JP | 08-064652 A | 3/1996 |
| JP | 2006-32110 A | 2/2006 |

(Continued)

OTHER PUBLICATIONS

Warabisako, Terunori et al., "Contactless Measurement of Wafer Lifetime by Free Carrier Infrared Absorption", Japanese Journal of Applied Physics, Jan. 1, 1982 (Jan. 1, 1982), pp. 557-560 (total 5 pages), XP55288629, Retrieved from the Internet: URL:http://iopscience.iop.org/article/10.7567/JJAPS.22S1.557/pdf.

(Continued)

*Primary Examiner* — Daniel R Miller
(74) *Attorney, Agent, or Firm* — Sughrue Mion, PLLC

(57) ABSTRACT

A photoelectric conversion element evaluation apparatus includes: a probe light source that irradiates a photoelectric conversion element as the object of measurement with probe light; a pump light source that irradiates the photoelectric conversion element being irradiated with the probe light with pulsed pump light; and a light receiving element that detects time dependency of a change in an amount of the probe light obtained from the photoelectric conversion element.

16 Claims, 7 Drawing Sheets

(56) References Cited

U.S. PATENT DOCUMENTS

2013/0222004 A1    8/2013  Nakanishi et al.
2013/0257472 A1*  10/2013  Kamieniecki .......... H01L 22/14
                                                  324/762.01

FOREIGN PATENT DOCUMENTS

JP        2012-209458 A    10/2012
JP        2013-174477 A     9/2013

OTHER PUBLICATIONS

Furube, Akihiro et al., "Femtosecond Diffuse Reflectance Transient Absorption for Dye-Sensitized Solar Cells under Operational Conditions: Effect of Electrolyte on Electron Injection", Journal of the American Chemical Society, vol. 132, No. 19, May 19, 2010 (May 19, 2010), pp. 6614-6615, XP55288688, US, ISSN: 0002-7862, DOI: 10.1021/ja910934y.

Cutolo, A. et al., "An optical technique to measure the bulk lifetime and the surface recombination velocity in silicon samples based on a laser diode probe system", Solid State Electronics, Elsevier Science Publishers, Barking, GB, vol. 42, No. 6, Jun. 1, 1998 (Jun. 1, 1998), pp. 1035-1038, XP004130787, ISSN: 0038-1101, DOI: 10.1016/S0038-1101(98)00125-7.

\* cited by examiner

PHOTOELECTRIC CONVERSION ELEMENT EVALUATION APPARATUS

CROSS-REFERENCE TO RELATED APPLICATION

This application claims priority from Japanese Patent Application No. 2015-033956 filed with the Japan Patent Office on Feb. 24, 2015, the entire content of which is hereby incorporated by reference.

BACKGROUND

1. Technical Field

An embodiment of the present disclosure relates to a photoelectric conversion element evaluation apparatus.

2. Description of the Related Art

For characteristics evaluation of a photoelectric conversion element (such as a solar cell), the current-voltage characteristic of the solar cell is measured to calculate its maximum output power (Pmax), for example. In addition, conversion efficiency (PCE) is calculated to provide a determination parameter. The conversion efficiency is computed by dividing the maximum output power by the irradiation output power of simulated sunlight and the area of the solar cell.

FIG. 11 is a block diagram of an example of a known solar cell evaluation apparatus. A solar cell 101 as the object of measurement is irradiated with simulated sunlight from a simulated sunlight source 102. Between the electrodes of the solar cell 101, a load 103 is connected in series with an ammeter 104. Between the electrodes of the solar cell 101, a voltmeter 105 is connected in parallel with the load 103.

The maximum output power Pmax and the conversion efficiency PCE of the solar cell 101 are calculated by determining a current-voltage characteristic curve as shown in FIG. 12. The current-voltage characteristic curve is determined as follows, for example. The solar cell 101 is irradiated with simulated sunlight from the simulated sunlight source 102. In this state, current is measured by the ammeter 104 and voltage is measured by the voltmeter 105 while the load 103 connected between the electrodes of the solar cell 101 is varied.

In FIG. 12, $\Delta Ioc$ is the amount of current decrease from the current in an open-circuit state. $\Delta Voc$ is the amount of voltage decrease from the voltage in the open-circuit state. A parallel resistance component Rsh in the solar cell 101 is determined according to the following expression:

$$Rsh = -\Delta Voc/\Delta Ioc$$

$\Delta Isc$ is the amount of current decrease from the current in a nearly short-circuited state. $\Delta Vsc$ is the amount of voltage decrease from the voltage in the nearly short-circuited state. A series resistance component Rs in the solar cell 101 is determined according to the following expression:

$$Rs = -\Delta Vsc/\Delta Isc$$

The conversion efficiency PCE can be determined according to the following expression:

$$PCE = Pmax/(E \cdot A)$$

where Pmax is the maximum output power, E is the irradiation power of the simulated sunlight with which the solar cell 101 is irradiated from the simulated sunlight source 102, and A is the area of the solar cell 101.

The current at the time of the maximum output power Pmax is a maximum output current Imax, and the voltage at the time of the maximum output power Pmax is a maximum output voltage Vmax.

JP-A-8-64652 describes an inspection method for evaluating the light emission output and response rate of a product while in the state of an epitaxial wafer.

SUMMARY

A photoelectric conversion element evaluation apparatus includes: a probe light source that irradiates a photoelectric conversion element as the object of measurement with probe light; a pump light source that irradiates the photoelectric conversion element being irradiated with the probe light with pulsed pump light; and a light receiving element that detects time dependency of a change in an amount of the probe light obtained from the photoelectric conversion element.

DESCRIPTION OF THE EMBODIMENTS

Figure 1:
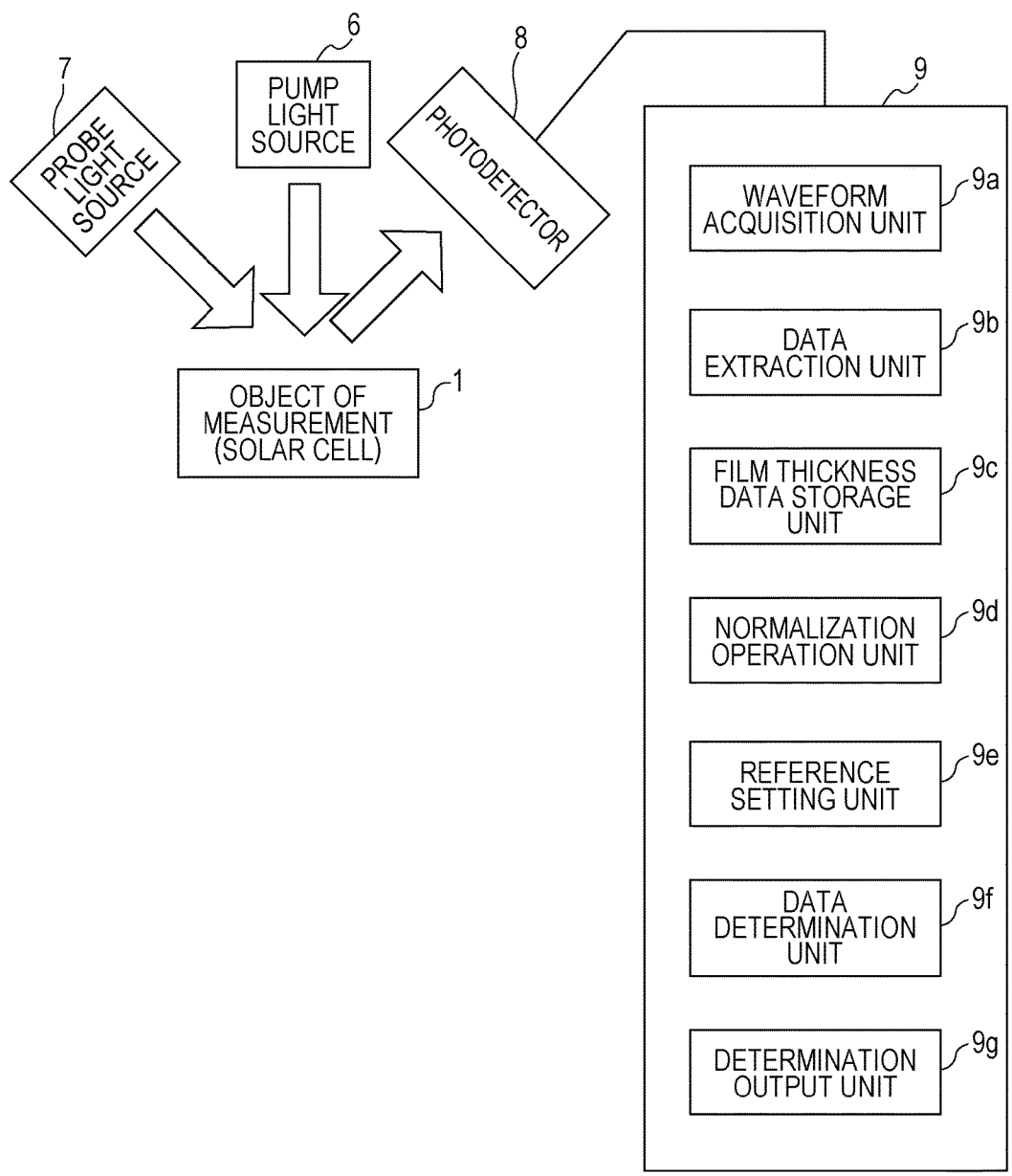
FIG. 1 is a conceptual block diagram illustrating an embodiment of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

As a solar cell manufacturing system, a roll-to-roll continuous production system is gaining attention. In this manufacturing system, rolled substrate sheets are successively wound up while a number of solar cells are being formed on the substrate sheets using printing technology.

Figure 11:
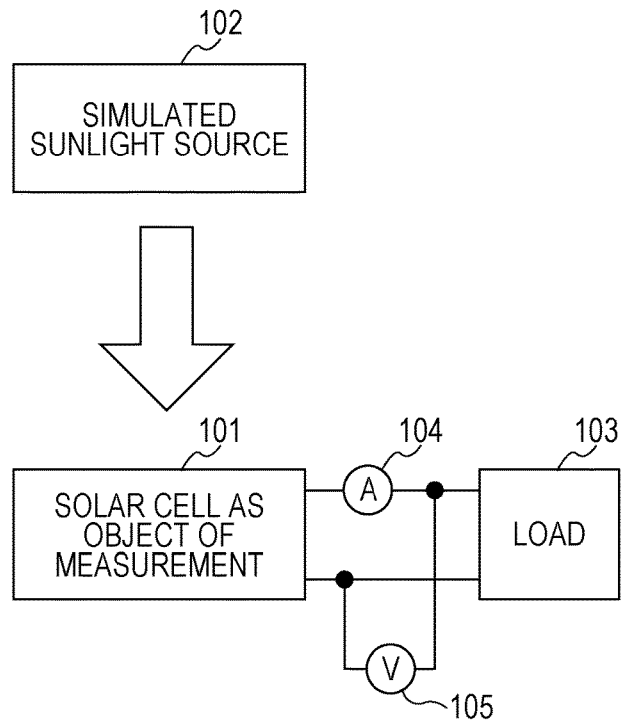
FIG. 11 is a block diagram illustrating an example of a known solar cell evaluation apparatus.
Figure 12:
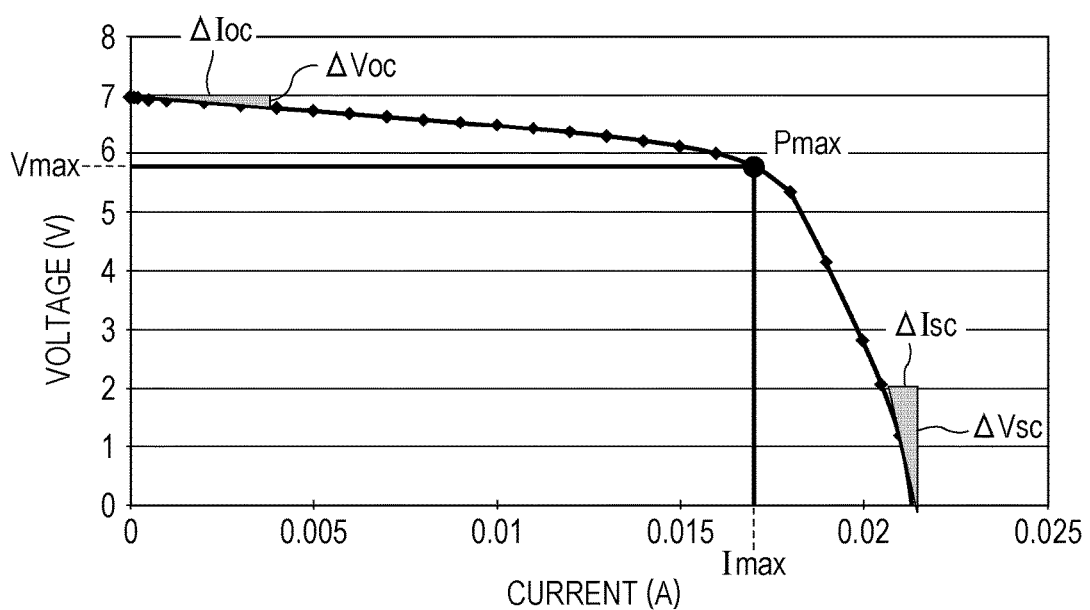
FIG. 12 is a diagram illustrating an example of a known current-voltage characteristic curve.

In the known evaluation apparatus as illustrated in FIG. 11, the load 103 connected between the electrodes of the solar cell 101 is varied during evaluation. Accordingly, electrical connection is required between the solar cell 101 and the load 103, which makes it difficult to use the known evaluation apparatus for evaluating solar cells produced by a roll-to-roll continuous production system.

In the roll-to-roll continuous production system, the solar cells as the object of measurement and evaluation are moved in an electrode-less state on the production line in a stage along the production process. Accordingly, it is difficult to bring a measuring probe pin into contact with the solar cells without damaging the solar cells.

Thus, with the known evaluation apparatus, it is difficult to detect a problem caused in a solar cell during the manufacturing process. Namely, with the known evaluation apparatus, it is difficult to determine the quality of the solar cells unless and until a roll is completely made.

As a result, all solar cells formed on a roll measuring several hundred meters in total length could end up being defective.

One object of the present disclosure is to provide a photoelectric conversion element evaluation apparatus as follows. The photoelectric conversion element evaluation apparatus is capable of accurately and precisely evaluating (determining) the characteristics of a photoelectric conversion element by measuring the characteristics of the photoelectric conversion element in a production line stage in a contactless manner, while preventing the photoelectric conversion element from being damaged.

A photoelectric conversion element evaluation apparatus (the evaluation apparatus) according to one aspect of the present disclosure, includes: a probe light source that irradiates a photoelectric conversion element as the object of measurement with probe light; a pump light source that irradiates the photoelectric conversion element being irradiated with the probe light with pulsed pump light; and a light receiving element that detects time dependency of a change in an amount of the probe light obtained from the photoelectric conversion element.

The evaluation apparatus may further include a data processing unit that evaluates a characteristic of the photoelectric conversion element on the basis of the time dependency of the change in the amount of light using a film thickness of the photoelectric conversion element.

In the evaluation apparatus, the photoelectric conversion element may be disposed on a production line for roll-to-roll continuous production.

In the evaluation apparatus, the probe light may have a pulse width including an irradiation period of the pump light and periods before and after the irradiation period.

The evaluation apparatus may further include a determination unit that estimates at least one of a photoelectric conversion efficiency maximum value of the photoelectric conversion element or a current leakage status in the photoelectric conversion element, on the basis of a ratio or difference between a first amount of change at a first point in time in the light amount of the probe light obtained from the photoelectric conversion element, and a second amount of change detected at a second point in time after the elapse of a certain time from the first point in time.

The evaluation apparatus may further include a determination unit that determines the quality of the photoelectric conversion element on the basis of a ratio or difference between a first amount of change at a first point in time in the light amount of the probe light obtained from the photoelectric conversion element, and a second amount of change detected at a second point in time after the elapse of a certain time from the first point in time.

The evaluation apparatus implements contactless measurement. Accordingly, the characteristics of a photoelectric conversion element in a production line stage (on a production line) of a roll-to-roll continuous production system, for example, can be accurately and precisely evaluated (determined) while preventing the photoelectric conversion element from being damaged. As a result, a defective element can be discovered early, whereby losses can be minimized and the yield can be improved.

In the following, the present disclosure will be described with reference to the drawings. FIG. 1 is a conceptual block diagram illustrating an embodiment of the present disclosure. As illustrated in FIG. 1, an evaluation apparatus (photoelectric conversion element evaluation apparatus) according to the present embodiment has a solar cell 1, a pump light source 6, a probe light source 7, a photodetector 8, and a signal processing unit 9.

The pump light source 6 irradiates the solar cell 1 with pulsed pump light. As the pump light source 6, a nanosecond pulsed laser is used, for example.

The probe light source 7 continuously irradiates the solar cell 1 with the probe light. As the probe light source 7, a semiconductor light-emitting element is used, for example. The solar cell 1 as the object of evaluation (i.e., the solar cell to be measured), is disposed on the production line for roll-to-roll continuous production, for example.

The photodetector (light receiving element) 8 detects the amount of change in the light amount of the probe light reflected by the solar cell 1 (reflected probe light; the probe light obtained from the solar cell 1) in real-time. Namely, the photodetector 8 detects the time dependency of the change in the amount of the probe light obtained from the solar cell 1. As the photodetector 8, a high-speed photodetector, such as a photodiode, is used, for example.

The signal processing unit 9 includes a waveform acquisition unit 9a; a data extraction unit 9b; a film thickness data storage unit 9c; a normalization operation unit 9d; a reference setting unit 9e; a data determination unit 9f; and a determination output unit 9g.

Figure 2:
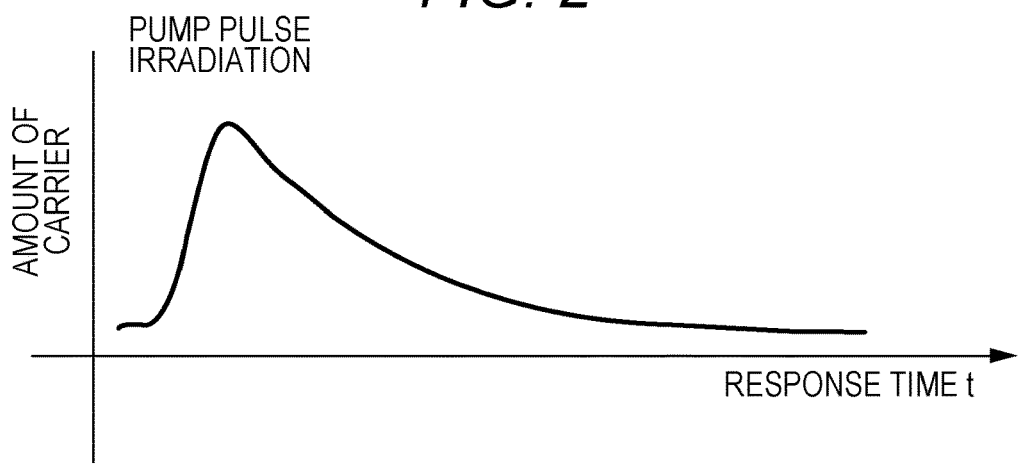
FIG. 2 is a conceptual diagram of carrier response by pulse irradiation of pump light.

As the solar cell 1 is irradiated with the pulsed pump light while the solar cell 1 is being continuously irradiated with the probe light, a carrier production and annihilation process appears in the solar cell 1 due to photoelectric conversion reaction, as illustrated in FIG. 2. FIG. 2 is a conceptual diagram of carrier response by pulse irradiation of pump light, where the vertical axis shows the amount of carrier and the horizontal axis shows the response time.

Figure 3:
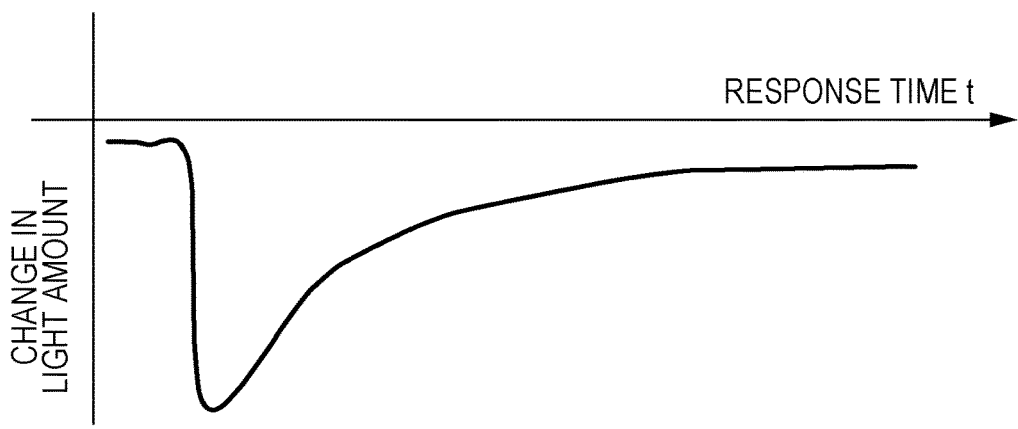
FIG. 3 is a conceptual diagram of a change in an amount of probe light in accordance with carrier response.

The optical intensity (light amount) of the reflected probe light is subject to the influence of variation in the light absorption process and the like corresponding to the carrier production status of the solar cell 1. Accordingly, the light amount of the reflected probe light varies as illustrated in FIG. 3. FIG. 3 is a conceptual diagram of the change in the amount of the reflected probe light in accordance with carrier response, where the vertical axis shows the change in the amount of light and the horizontal axis shows the response time.

As will be seen from the above, by detecting the amount of change in the light amount of the reflected probe light in real-time, and measuring the temporal shift in the amount of carrier, the carrier production and annihilation status can be determined.

Figure 4:
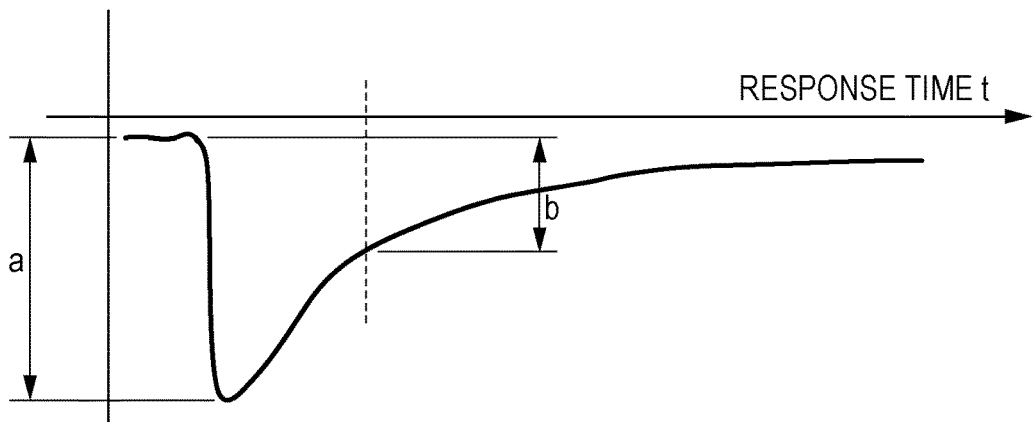
FIG. 4 is an illustrative diagram of a parameter for evaluating the characteristics of a solar cell.

In order to ensure adaptation to a continuous production process, such as a roll-to-roll process, in which the solar cells are moving, it is preferable to shorten the evaluation time. Accordingly, in order to shorten the calculation time, in the present embodiment, a carrier lifetime acquisition method, which is a typical technique used for evaluating a temporal shift, may not be used. In the present embodiment, as illustrated in FIG. 4, a peak value a (a first amount of change at a first point in time) of the amount of change in the light amount of the reflected probe light, and an amount of change b (a second amount of change) in the light amount of the reflected probe light at a point in time (a second point in time) after the elapse of a certain time from the point in time (the first point in time) corresponding to the peak value a, are used as determination references. FIG. 4 is an illustrative diagram of a parameter for solar cell characteristics evaluation.

In FIG. 4, the solar cell having a large peak value a and a large amount of change b is a non-defective item with high efficiency as a solar cell. The peak value a corresponds to the amount of carrier produced. That the peak value a is large indicates that a large amount of carrier has been produced. The amount of change b corresponds to the degree of carrier annihilation. That the amount of change b is small indicates that a large amount of carrier has been annihilated by leakage and the like. Appropriate values of the peak value a and the amount of change b may vary depending on material and process conditions and the like. Accordingly, the material and process conditions may be adjusted as needed.

The probe light is not limited to continuous light and may be pulse light. When the probe light is pulse light, the pulse width of the probe light is made sufficient wider than the pulsed pump light (pump pulse) from the pump light source 6. For example, the probe light has a pulse width including a pump pulse irradiation period and periods before and after the irradiation period. Further, as the probe light source 7, a light source capable of stabilizing the probe light intensity during, before, and after pump pulse irradiation is used.

Figure 5A:
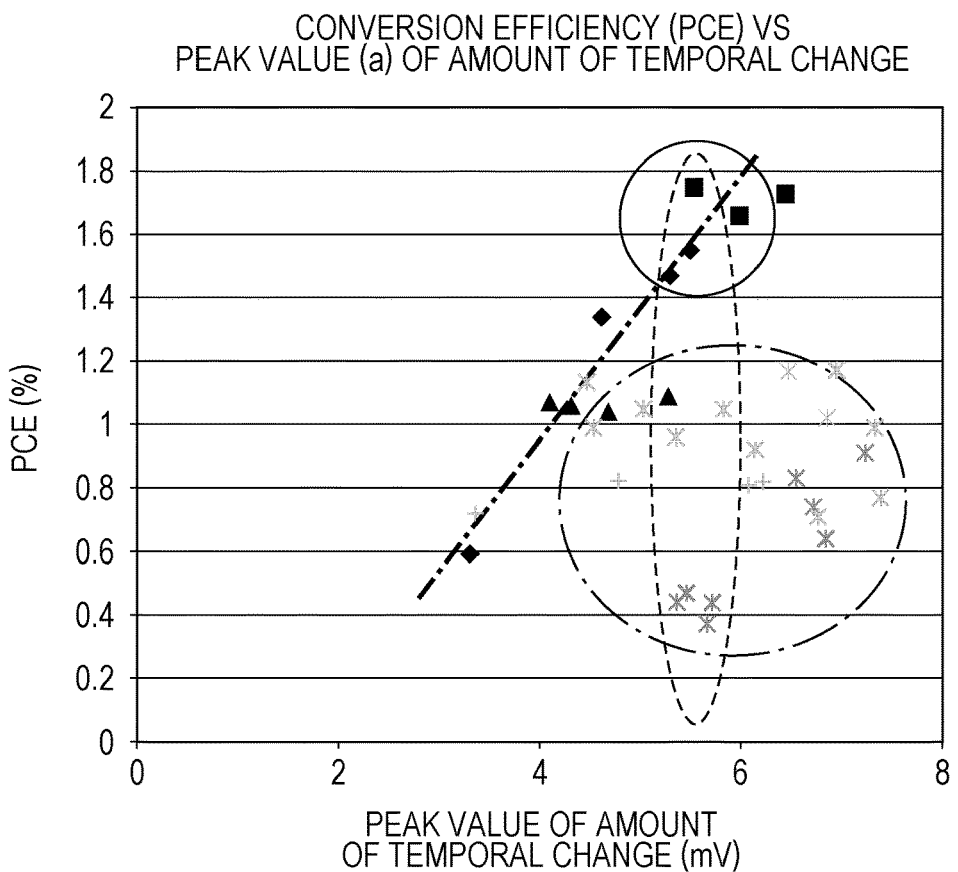
FIGS. 5A and 5B illustrate characteristics measurement examples of a solar cell.
Figure 5B:
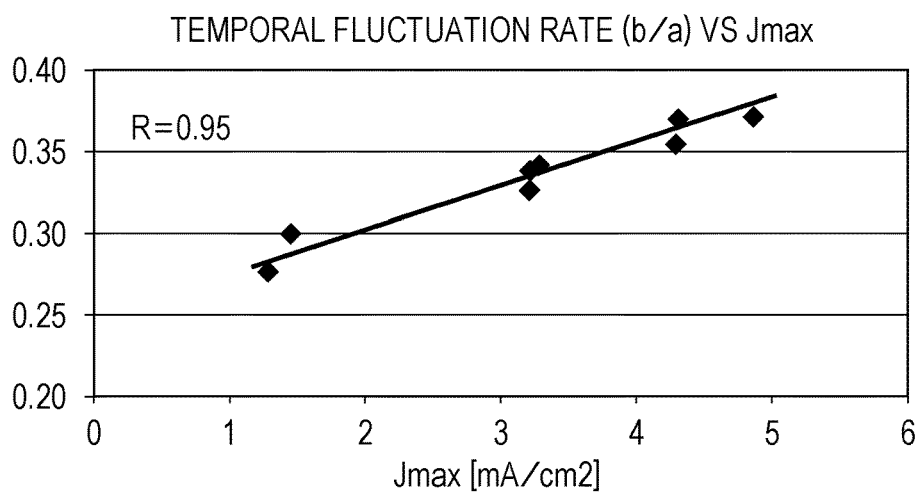

FIGS. 5A and 5B illustrate solar cell characteristics measurement examples. FIG. 5A shows the relationship between conversion efficiency and the peak value of the amount of temporal change (the above-described peak value a). FIG. 5B shows the relationship between temporal fluctuation rate and the maximum conversion output current (the maximum output current) Imax. The photoelectric conversion efficiency of a solar cell is inherently related to the amount of carrier produced. The dashed straight line in FIG. 5A indicates the correlation between photoelectric conversion efficiency and the amount of carrier produced. That the photoelectric conversion efficiency of a solar cell is outside the line means that the solar cell has some kind of problem.

When the dashed straight line of FIG. 5A is used, as an example of determination, the solar cells having PCE of 1% or more can be selected by setting the peak value a at 4 mV or above. However, in reality, some solar cells have poor photoelectric conversion efficiency even though the cells have sufficient amounts of carrier produced, such as the solar cells within the dashed line circle deviating from the dashed straight line. In such solar cells, it is believed that the carrier does not readily produce a current, i.e., that the Imax is poor.

The signal processing unit (determination unit) 9 extracts sample data enclosed in the broken line ellipse in FIG. 5A in which the peak value a corresponding to the amount of carrier produced is around 5.5 mV. Further, the signal processing unit 9 acquires, as the amount of change b, the amount of change in the light amount of the reflected probe light at the point in time after the elapse of 100 nsec from the point in time corresponding to the peak value a. In this case, between the maximum output current Imax and b/a, there is a high correlation, as illustrated in FIG. 5B. In this case, the signal processing unit 9 can select, from the devices (solar cells) in the range of the black broken line of FIG. 5A, only the non-defective items corresponding to the inside of the solid line circle of FIG. 5A by selecting those having the b/a of 0.35 or more.

The conversion efficiency PCE of the solar cell 1 can be determined according to the following expression:

$$PCE = Pmax/(E \cdot A)$$

where Pmax is the maximum output power, E is the irradiation power of the light (such as pump light) with which the solar cell 1 is irradiated, and A is the area of the solar cell 1.

The maximum output current Imax is the current at the time of the maximum output power Pmax. The voltage at the time of the maximum output power Pmax is the maximum output voltage Vmax.

The waveform acquisition unit 9a of the signal processing unit 9 acquires a waveform of the change in the amount of the reflected probe light due to carrier response as illustrated in FIG. 3.

The data extraction unit 9b extracts, from the acquired waveform of FIG. 3, the peak value a of the amount of change in the light amount of the reflected probe light, and the amount of change b at the point in time after the elapse of a certain time from the point in time corresponding to the peak value a, as illustrated in FIG. 4.

In the film thickness data storage unit 9c, film thickness data of the solar cell 1 as the object of measurement and evaluation are stored.

The normalization operation unit 9d performs calculation for normalizing the measured temporal shift in the carrier (the change in the amount of the reflected probe light) on the basis of the film thickness data stored in the film thickness data storage unit 9c.

The reference setting unit 9e sets a predetermined reference value. The predetermined reference value provides the reference for determining the appropriateness of the amount of change b extracted by the data extraction unit 9b.

The data determination unit 9f, on the basis of the reference value set by the reference setting unit 9e, determines the appropriateness of the amount of change b extracted by the data extraction unit 9b.

The determination output unit 9g outputs the result of determination by the data determination unit 9f to the outside as a determination result for the solar cell 1 as the object of measurement.

In the evaluation apparatus according to the present embodiment, as the determination technique, a spot evaluation narrowing down to two points in time, rather than lifetime evaluation, is introduced. Thereby, the calculation time can be significantly reduced, whereby high-speed measurement can be handled.

In the evaluation apparatus according to the present embodiment, the influence of internal current leakage can be estimated. Thus, a solar cell that may possibly become degraded early in the future can be eliminated.

It is known that the conversion efficiency of the solar cell 1 is eventually dependent on the degree (probability) of carrier transport to the both electrodes after carrier production.

Figure 6:
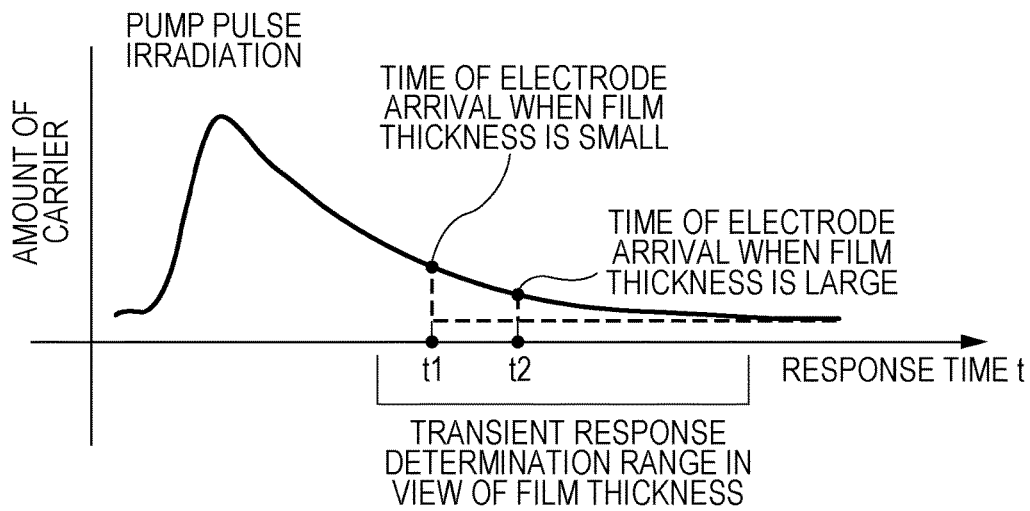
FIG. 6 is a characteristics example diagram illustrating the relationship between film thickness and carrier annihilation.

FIG. 6 is a characteristics example diagram illustrating the relationship between film thickness and carrier annihilation, where time t1 indicates the electrode arrival time when the film thickness is small, while time t2 indicates the electrode arrival time when the film thickness is large. For example, when the film thickness of the solar cell 1 is sufficiently large, the amount of absorption of pump light is increased, whereby a large amount of carrier is produced. However, the amount of carrier is also increased that fails to reach the electrodes and becomes annihilated.

When the film thickness of the solar cell 1 is sufficiently large, the value of the peak value a (see FIG. 4) of the amount of change is increased, whereby the value of the amount of change b at a point in time after the elapse of a certain time from the point in time corresponding to the peak value a is also increased to a certain extent. However, the carrier does not easily reach the electrodes, and therefore does not readily produce a current. Such solar cell 1 has poor conversion efficiency and yet the peak value a and the value of the amount of change b of the solar cell are somewhat satisfactory. As a result, the solar cell 1 could be determined to be a non-defective item.

In the present embodiment, in order to eliminate the problem, the signal processing unit 9 is provided with the film thickness data storage unit 9c and the normalization operation unit 9d, as illustrated in FIG. 1. By the film thickness data storage unit 9c and the normalization operation unit 9d, the film thickness is reflected in the evaluation parameter, whereby more appropriate quality determination can be made.

As described above, when the solar cell 1 is irradiated with the pulsed pump light from the pump light source 6 while the solar cell 1 is continuously irradiated with the probe light from the probe light source 7, the carrier production and annihilation process, as illustrated in FIG. 2, appears in the solar cell 1 due to the photoelectric conversion reaction. The optical intensity (light amount) of the reflected probe light is changed by the influence of variation in the light absorption process and the like corresponding to the carrier production status of the solar cell 1, as illustrated in FIGS. 3 and 6.

Accordingly, by detecting the amount of change in the light amount of the reflected probe light in real-time, and thereby measuring the temporal shift in the amount of carrier, the carrier production and annihilation status can be learned. Generally, the parameter indicating the carrier production and annihilation status is referred to as carrier lifetime, which is expressed by the time that elapses before the amount of carrier becomes 1/e the amount as produced.

In the case of the film thickness of an actual device (solar cell 1), the lifetime is sufficiently long, so that the carrier reaches the electrodes before annihilation. Accordingly, based on the data obtained from measurement, it appears as if the lifetime is changed in conjunction with the film thickness in a simulated manner. Thus, by normalizing the measured temporal shift in the carrier using film thickness, quality selection of the completed solar cell 1 can be performed more accurately.

The broken line portion of FIG. 6 indicates an actual change in the amount of carrier depending on the difference in film thickness, showing that the carrier is annihilated at the point in time of arrival to the electrodes. However, this portion becomes slowly attenuated due to the S/N of the measurement apparatus, as indicated by the solid line, resulting in an unclear electrode arrival position. As a result, the carrier lifetime derived from the measurement result is changed from the actual value due to the influence of the electrode arrival time. It should be noted that FIG. 6 is drawn with the difference emphasized for the sake of clarity.

Specifically, when the film thickness is small, the carrier lifetime appears to be short, while when the film thickness is large, the carrier lifetime appears to be long. Accordingly, in the present embodiment, the normalization operation unit 9d provided in the signal processing unit 9 performs a calculation for normalizing, using the film thickness data stored in the film thickness data storage unit 9c, the carrier lifetime determined from measurement.

Figure 7:
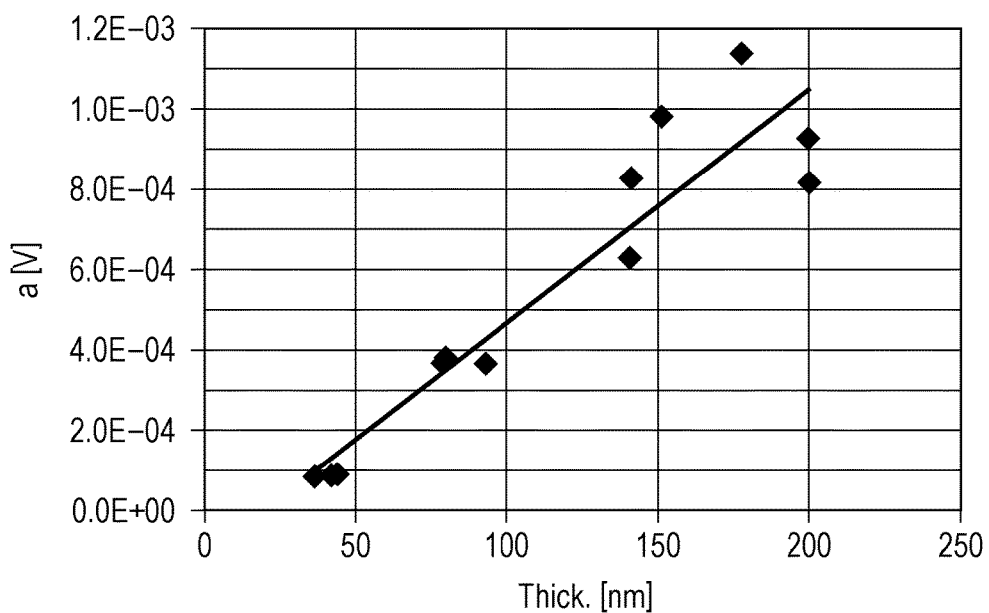
FIG. 7 is a characteristics example diagram illustrating the relationship between film thickness and the amount of carrier produced.

FIG. 7 is a characteristics example diagram indicating the relationship between film thickness and the amount of carrier produced. Under the process condition that the anneal temperature that influences the carrier lifetime is controlled in a certain way, a plurality of samples that differ only in film thickness is prepared. FIG. 7 shows the plot of the amount of change (the peak value a in FIG. 4) in the reflected probe light amount corresponding to the amount of carrier produced in the samples. According to the characteristics diagram of FIG. 7, it can be confirmed that the amount of change (the peak value a) in the reflected probe light is increased in proportion to film thickness. Because the peak value a of the reflected probe light amount is converted into an electric signal, the peak value a is expressed in voltage.

Figure 8:
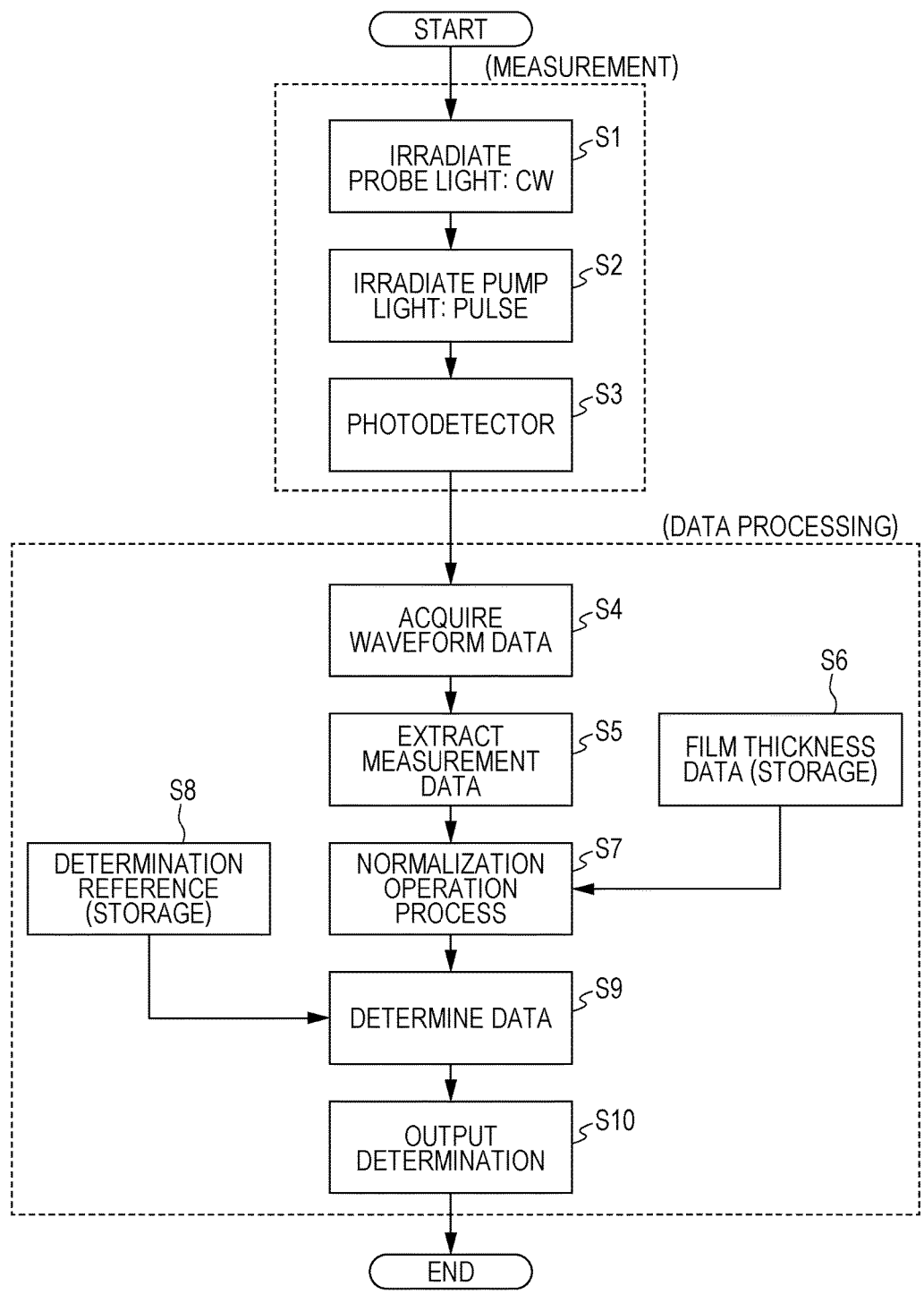
FIG. 8 is a flowchart for describing the flow of operation of an apparatus as a whole configured as illustrated in FIG. 1.

FIG. 8 is a flowchart illustrating the flow of operation of the evaluation apparatus as a whole configured as illustrated in FIG. 1. The operation can be generally divided into a measurement mode A of the first half and a data processing mode B of the latter half by the signal processing unit (data processing unit) 9.

First, the photoelectric conversion element as the object of measurement (solar cell) 1 is continuously irradiated with the probe light from the probe light source 7 (step S1). In this state, the pump light source 6 emits pulsed pump light (step S2). The amount of change in the light amount of the reflected probe light reflected by the solar cell 1 is detected in real-time by the photodetector 8 (step S3). The operation from step S1 to step S3 constitutes the measurement mode A.

Thereafter, the waveform acquisition unit 9a of the signal processing unit 9 acquires, from the output signal from the photodetector 8, waveform data of the change in the amount of the reflected probe light (step S4). The data extraction unit 9b extracts from the acquired waveform data measurement data indicating a desired amount of change b (step S5). The normalization operation unit 9d reads film thickness data from the film thickness data storage unit 9c (step S6). The normalization operation unit 9d, using the read film thickness data, performs operation (normalization operation) for normalizing the measurement data (the amount of change b) extracted by the data extraction unit 9b (step S7).

The data determination unit 9f then reads the reference value previously set and stored by the reference setting unit 9e (step S8). The data determination unit 9f, using the reference value, determines the appropriateness of the amount of change b (measurement data) extracted by the data extraction unit 9b for which the normalization operation has been performed by the normalization operation unit 9d (step S9). The data determination unit 9f outputs the determination result to the outside via the determination output unit 9g (step S10). The operation from step S4 to step S10 constitutes the data processing mode B. Thus, the signal processing unit 9 evaluates the characteristics of the solar cell 1 using the film thickness of the solar cell 1 and on the basis of the time dependency (waveform data) of the change in the amount of the probe light from the solar cell 1.

By executing the series of operations, the characteristics of the photoelectric conversion element (solar cell 1) on a production line stage (on a production line) of a roll-to-roll continuous production system can be accurately and precisely evaluated (determined) while preventing the photoelectric conversion element from being damaged. As a result, the defective element can be discovered early, whereby losses can be minimized and the yield can be improved.

Figure 9:
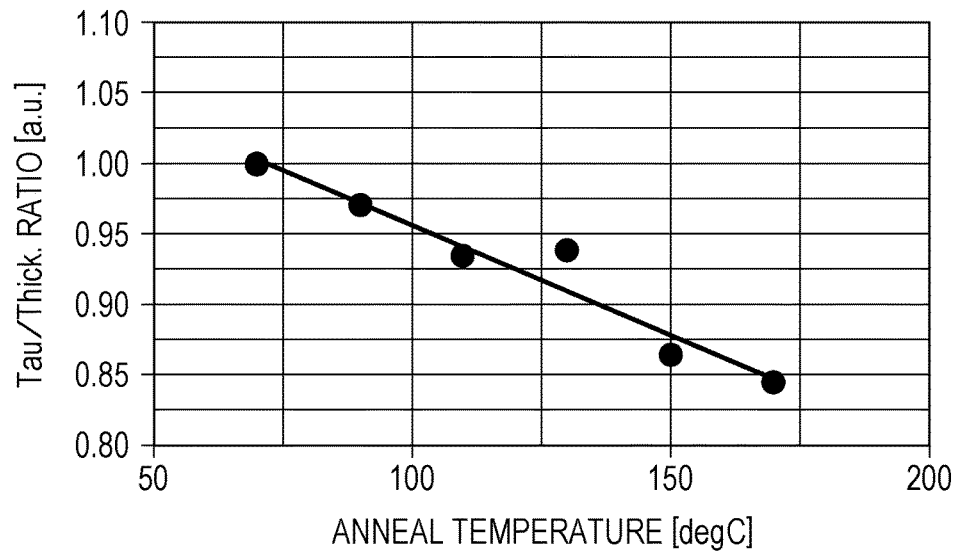
FIG. 9 is a characteristics diagram illustrating an actual measurement example of the relationship between anneal temperature and carrier lifetime/film thickness.

FIG. 9 is a characteristics diagram illustrating an actual measurement example of the relationship between anneal temperature and carrier lifetime/film thickness. As will be seen from the characteristics of FIG. 9, the value of the carrier lifetime that has been normalized using film thickness shows high correlation with respect to the anneal temperature.

In an organic solar cell, anneal temperature and crystallinity are related to each other. With regard to anneal temperature, it has been reported that temperatures on the order of 100° C. to 130° C. are proper. In the example of FIG. 9, it is preferable that the value of lifetime/film thickness be on the order of 0.9 to 0.95. Accordingly, the sample (solar cell 1) of which the value of lifetime/film thickness is outside the above range has a high likelihood of having a crystallinity problem, and can be determined to be of inappropriate quality.

In the embodiment, an example has been described in which quality determination is made on the basis of the ratio of the amount of change in the reflected probe light amount (b/a). Instead, quality determination may be made on the basis of the difference in the amount of change in the reflected probe light amount.

Alternatively, the signal processing unit 9 may determine the quality of the solar cell 1 on the basis of the ratio or difference between the first amount of change at the first point in time (the peak value a) in the light amount of the probe light (the reflected probe light) obtained from the solar cell 1 (the photoelectric conversion element), and the second amount of change detected at the second point in time (the amount of change b) after the elapse of a certain time from the first point in time.

The signal processing unit 9 may estimate at least one of the photoelectric conversion efficiency maximum value or the status of current leakage in the solar cell 1 on the basis of the ratio or difference between the first amount of change (peak value a) and the second amount of change (the amount of change b).

Figure 10:
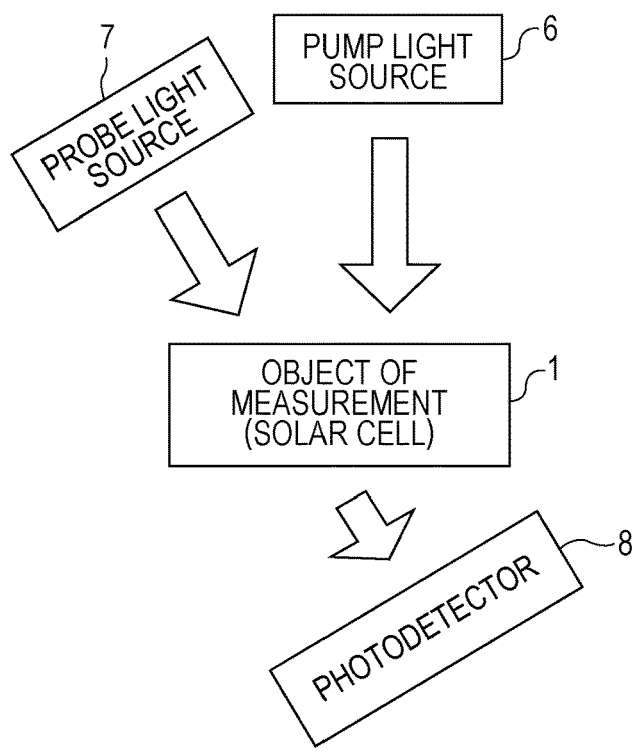
FIG. 10 is a conceptual block diagram illustrating another embodiment of the present disclosure.

The measurement system of the evaluation apparatus according to the present embodiment is not limited to the reflected light measurement system illustrated in FIG. 1. The measurement system of the evaluation apparatus according to the present embodiment may be a transmitted light measurement system illustrated in FIG. 10. In this measurement system, the pump light source 6 and the probe light source 7 are disposed opposite the photodetector 8 across the solar cell 1 as the object of measurement. For example, the photodetector 8 detects, in real-time, the amount of change in light amount of the probe light (transmitted probe light; probe light obtained from the solar cell 1) that has passed through the solar cell 1. For example, the signal processing unit 9 extracts the peak value a and the amount of change b similarly to when the reflected probe light is used, and determines the quality of the solar cell 1 using the film thickness data.

Further, in the embodiment, the example has been described in which the solar cell characteristics are measured. However, an embodiment of the present disclosure may be applied for characteristics measurement of a photoelectric conversion element other than a solar cell.

As described above, in the evaluation apparatus (evaluate method) according to the present embodiment, by measuring the characteristics of the photoelectric conversion element in a contactless manner, the characteristics of the photoelectric conversion element can be evaluated (determined) precisely while preventing the photoelectric conversion element from being damaged. For example, by applying the evaluation apparatus (evaluate method) according to the present embodiment to a production line for a photoelectric conversion element produced by a roll-to-roll process, a defective element can be discovered early. As a result, losses can be minimized and the yield can be improved.

In the data processing mode B, the data determination unit 9f may determine whether b/a is a predetermined value (such as 0.35) or more, using a normalized amount of change b. The data determination unit 9f may output the determination result to the outside via the determination output unit 9g. Alternatively, the data determination unit 9f may calculate the value of a-b using the normalized amount of change b, determine the quality of the solar cell 1 on the basis of the value, and output the determination result to the outside.

In the data processing mode B, the following process may be executed.

The waveform acquisition unit 9a of the signal processing unit 9 acquires, from the output signal from the photodetector 8, waveform data of the change in the amount of the reflected probe light (step S4). The data extraction unit 9b extracts, from the acquired waveform data, measurement data indicating the peak value a (step S5). The normalization operation unit 9d reads film thickness data from the film thickness data storage unit 9c (step S6). The normalization operation unit 9d, using the read film thickness data, performs operation (normalization operation) for normalizing the measurement data (the peak value a) extracted by the data extraction unit 9b (step S7).

Then, the data determination unit 9f reads the reference value previously set and stored by the reference setting unit 9e (step S8). The data determination unit 9f, using the reference value, determines the appropriateness of the peak value a (measurement data) extracted by the data extraction unit 9b for which normalization operation has been performed by the normalization operation unit 9d (step S9). The data determination unit 9f outputs the determination result to the outside as the quality of the solar cell 1 via the determination output unit 9g (step S10).

Further, in the data processing mode B, the following process may be executed.

The waveform acquisition unit 9a of the signal processing unit 9 acquires, from the output signal from the photodetector 8, waveform data of the change in the amount of the reflected probe light (step S4). The data extraction unit 9b extracts, from the acquired waveform data, measurement data indicating the peak value a and the amount of change b (step S5). The normalization operation unit 9d reads film thickness data from the film thickness data storage unit 9c (step S6). The normalization operation unit 9d, using the read film thickness data, performs operation (normalization operation) for normalizing the measurement data (the peak value a and the amount of change b) extracted by the data extraction unit 9b (step S7).

Thereafter, the data determination unit 9f reads the reference value previously set and stored by the reference setting unit 9e (step S8). The data determination unit 9f, using the reference value, determines the appropriateness of the peak value a and the amount of change b (measurement data) extracted by the data extraction unit 9b for which normalization operation has been performed by the normalization operation unit 9d (step S9). Namely, the data determination unit 9f determines whether b/a is a predetermined value (such as 0.35) or more. The data determination unit 9f outputs the determination result to the outside via the determination output unit 9g (step S10). Alternatively, the data determination unit 9f may calculate the value of a–b, determine the quality of the solar cell 1 on the basis of the value, and output the determination result to the outside.

An embodiment of the present disclosure may be said to relate to a photoelectric conversion element evaluation apparatus, or more specifically, to an evaluation apparatus in a photoelectric conversion element production line process.

The photodetector 8 may be configured to detect in real-time the amount of change in the probe light with which the solar cell 1 is irradiated. In an embodiment of the present disclosure, in order to shorten the calculation time, the peak value a of the amount of change and the amount of change b after the elapse of a certain time point in time from the peak value a may be used as determination references, as illustrated in FIG. 4.

The values of the peak value a and the amount of change b may be adjusted as needed as the appropriate values may vary depending on material or process conditions. The dashed straight line in FIG. 5A indicates the correlation between photoelectric conversion efficiency and the amount of carrier produced, and the devices deviating from the line can be said to have some kind of problem.

When the sample data enclosed in the broken line ellipse in FIG. 5A in which the peak value a of the amount of change corresponding to the amount of carrier produced is around 5.5 mV are extracted, and when the amount of change b after the elapse of a certain time from the peak value is evaluated at the position of 100 nsec, it can be said that the values of Imax and b/a have a high correlation, as illustrated in FIG. 5B. In this case, by setting b/a to be 0.35 or more, it becomes possible to select from the devices in the range of the black broken line of FIG. 5A only the non-defective items in the solid line circle portion of FIG. 5A.

Embodiments of the present disclosure may include the following first to fourth photoelectric conversion element evaluation apparatuses.

A first photoelectric conversion element evaluation apparatus is a photoelectric conversion element evaluation apparatus that performs evaluation of a photoelectric conversion element in a contactless manner, the apparatus including: a probe light source that irradiates the photoelectric conversion element as the object of measurement with probe light; a pump light source that irradiates the photoelectric conversion element being irradiated with probe light with pulsed pump light; a light receiving element that detects time dependency of a change in an amount of the probe light with which the photoelectric conversion element is irradiated; and a data processing unit that performs evaluation and determination of the characteristics of the photoelectric conversion element on the basis of a temporal shift in the amount of carrier as a result of irradiation of the pump light, using a value of the film thickness of the photoelectric conversion element as a parameter.

In a second photoelectric conversion element evaluation apparatus according to the first photoelectric conversion element evaluation apparatus, the photoelectric conversion element is in a production line stage of a roll-to-roll continuous production process.

In a third photoelectric conversion element evaluation apparatus according to the first or second photoelectric conversion element evaluation apparatus, the probe light has a pulse width including an irradiation period of the pump light and periods before and after the irradiation period.

In a fourth photoelectric conversion element evaluation apparatus according to any of the first to third photoelectric conversion element evaluation apparatuses, at least one of a photoelectric conversion efficiency maximum value or a status determination of an intra-element current leakage is estimated using, as a determination reference, a ratio or difference between the amount of change at a certain point in time that is detected by irradiating the photoelectric conversion element with the pulsed pump light while being continuously irradiated with the probe light, and the amount of change detected after the elapse of a certain time, The first to fourth photoelectric conversion element evaluation apparatuses, which perform contactless measurement, can perform characteristics evaluation and determination accurately and precisely in a production line stage of a roll-to-roll continuous production system without damaging the photoelectric conversion element, whereby a defective element can be discovered early, enabling an improvement in the yield while minimizing losses.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A photoelectric conversion element evaluation apparatus comprising:
    a probe light source that irradiates a photoelectric conversion element as the object of measurement with probe light;
    a pump light source that irradiates the photoelectric conversion element being irradiated with the probe light with pulsed pump light;
    a light receiving element that detects time dependency of a change in an amount of the probe light reflected from the photoelectric conversion element; and
    a data processing circuit that evaluates a characteristic of the photoelectric conversion element based on the time dependency of the change in the amount of light and a film thickness of the photoelectric conversion element.

2. The photoelectric conversion element evaluation apparatus according claim 1, wherein the photoelectric conversion element is disposed on a production line for roll-to-roll continuous production.

3. The photoelectric conversion element evaluation apparatus according to claim 1, wherein
    the probe light is pulsed light that has a pulse width including an irradiation period of the pulsed pump light and periods before and after the irradiation period.

4. The photoelectric conversion element evaluation apparatus according to claim 2, wherein the probe light is pulsed light that has a pulse width including an irradiation period of the pulsed pump light and periods before and after the irradiation period.

5. The photoelectric conversion element evaluation apparatus according to claim 1, further comprising a determination circuit that estimates at least one of a photoelectric conversion efficiency maximum value of the photoelectric conversion element or a current leakage status in the photoelectric conversion element, on the basis of a ratio or difference between a first amount of change at a first point in time in the light amount of the probe light obtained from the photoelectric conversion element, and a second amount of change detected at a second point in time after the elapse of a certain time from the first point in time.

6. The photoelectric conversion element evaluation apparatus according to claim 1, further comprising a determination circuit that determines the quality of the photoelectric conversion element on the basis of a ratio or difference between a first amount of change at a first point in time in the light amount of the probe light obtained from the photoelectric conversion element, and a second amount of change detected at a second point in time after the elapse of a certain time from the first point in time.

7. An apparatus comprising:
a probe source that irradiates a thin film solar cell with probe light;
a pump source that irradiates the thin film solar cell being irradiated with the probe light, with pulsed pump light;
a photodetector that detects a time dependency of a change in an amount of the probe light reflected from the thin film solar cell; and
a circuit that determines whether the thin film solar cell is defective based on the amount of the probe light that is detected and a film thickness of the thin film solar cell.

8. The apparatus according to claim 7, wherein the pump source is a nanosecond pulsed laser.

9. The apparatus according to claim 8, wherein the probe source is a semiconductor light-emitting element.

10. The apparatus according to claim 7, wherein the probe source is a semiconductor light-emitting element.

11. The apparatus according to claim 7, wherein the probe light is pulsed light having a pulse width greater than a pulse width of the pulsed pump light.

12. An apparatus comprising:
a probe source that individually irradiates each of a plurality of thin film solar cells printed on a rolled substrate with probe light;
a pump source that irradiates an irradiated solar cell of the plurality of thin film solar cells that is being irradiated with the probe light, with pulsed pump light;
a photodetector that detects a time dependency of a change in an amount of the probe light reflected from the irradiated solar cell; and
a circuit that determines whether the irradiated solar cell of the plurality of thin film solar cells is defective based on the amount of the probe light that is detected and a film thickness of thin film solar cells.

13. The apparatus according to claim 12, wherein the pump source is a nanosecond pulsed laser.

14. The apparatus according to claim 13, wherein the probe source is a semiconductor light-emitting element.

15. The apparatus according to claim 12, wherein the probe source is a semiconductor light-emitting element.

16. The apparatus according to claim 12, wherein the probe light is pulsed light having a pulse width greater than a pulse width of the pulsed pump light.

* * * * *